(12) United States Patent
Zimmermann et al.

(10) Patent No.: US 10,408,791 B2
(45) Date of Patent: Sep. 10, 2019

(54) METHOD FOR OPERATING AN ION GATE, DEVICE HAVING AN ION TRANSPORT REGION, AND COMPUTER PROGRAM

(71) Applicant: Gottfried Wilhelm Leibniz Universitaet Hannover, Hannover (DE)

(72) Inventors: Stefan Zimmermann, Burgwedel (DE); Ansgar Kirk, Hannover (DE)

(73) Assignee: GOTTFRIED WILELM LEIBNIZ UNIVERSITAET HANNOVER, Hannover (DE)

( * ) Notice: Subject to any disclaimer, the term of this patent is extended or adjusted under 35 U.S.C. 154(b) by 0 days.

(21) Appl. No.: 15/749,938

(22) PCT Filed: Aug. 2, 2016

(86) PCT No.: PCT/EP2016/068424
§ 371 (c)(1),
(2) Date: Feb. 2, 2018

(87) PCT Pub. No.: WO2017/021406
PCT Pub. Date: Feb. 9, 2017

(65) Prior Publication Data
US 2018/0224401 A1 Aug. 9, 2018

(30) Foreign Application Priority Data
Aug. 5, 2015 (DE) .................. 10 2015 112 869

(51) Int. Cl.
*G01N 27/62* (2006.01)
*H01J 49/00* (2006.01)
(Continued)

(52) U.S. Cl.
CPC ........ *G01N 27/622* (2013.01); *H01J 49/0027* (2013.01); *H01J 49/061* (2013.01); *H01J 49/10* (2013.01)

(58) Field of Classification Search
CPC ... G01N 27/62; G01N 27/622; H01J 49/0027; H01J 49/0031; H01J 49/06; H01J 49/061; H01J 49/10
See application file for complete search history.

(56) References Cited

U.S. PATENT DOCUMENTS

2003/0141446 A1 7/2003 Blanchard
2005/0205775 A1 9/2005 Bromberg et al.
(Continued)

FOREIGN PATENT DOCUMENTS

DE 11 2009 001 895 B4 7/2013
GB 2464605 A 4/2010
WO 2015/091146 A1 6/2015

OTHER PUBLICATIONS

Langejuergen et al.; "High Kinetic Energy Ion Mobility Spectrometer: Quantitative Analysis of Gas Mixtures with Ion Mobility Spectrometry"; Analytical Chemistry, vol. 86, No. 14, Jun. 17, 2014, pp. 7023-7032.

*Primary Examiner* — David E Smith
(74) *Attorney, Agent, or Firm* — W&C IP

(57) ABSTRACT

The invention relates to a method for operating an ion gate having at least a first, a second, and a third electrode, which are arranged one after the other in an intended drifting direction of ions to be influenced by the ion gate, in such a way that the second electrode is arranged after the first electrode and the third electrode is arranged after the second electrode in the drifting direction, wherein the ion gate can be switched between a closed state, in which ions cannot drift through the ion gate in the intended drifting direction, and an open state, in which ions can drift through the ion (Continued)

Figure 1:
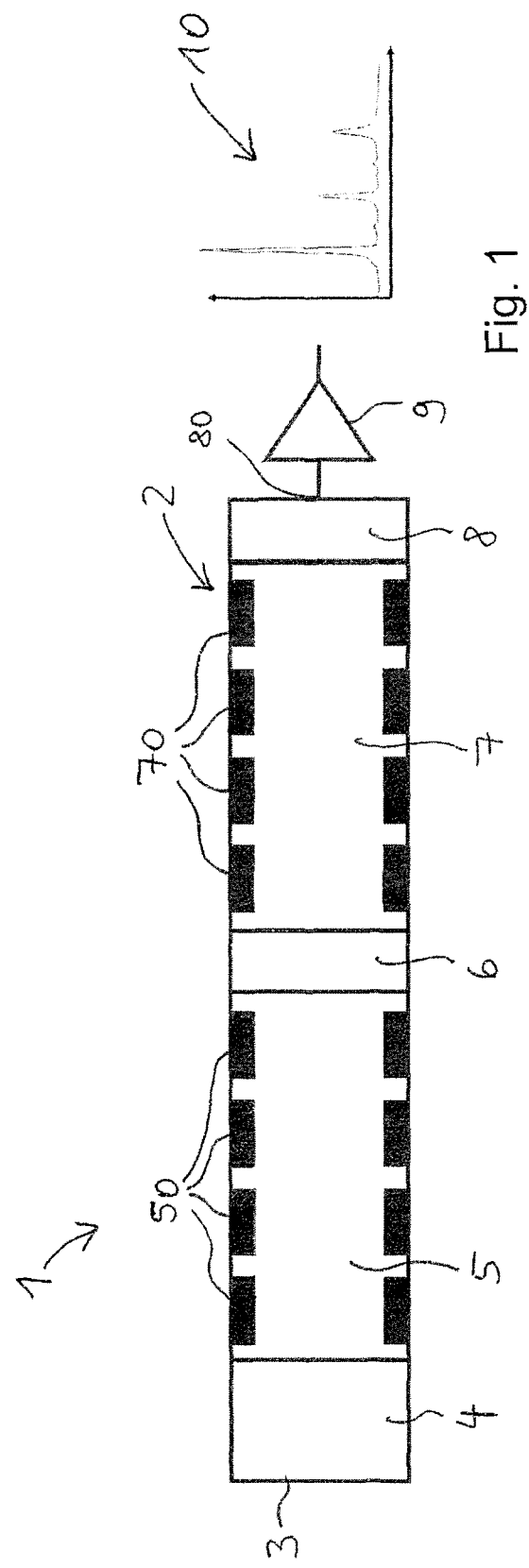

gate in the intended drifting direction, by applying potentials that alternate over time to one or more of the electrodes mentioned above, wherein, in a switching cycle of the ion gate, which comprises the open state and the closed state of the ion gate, two different closed states of the ion gate are produced in that, in a first closed state, the ion gate is closed by applying a first potential difference between the second and the third electrodes and, in a second closed state, the ion gate is closed by applying a second potential difference between the first and the second electrodes. The invention further relates to a device having an ion transport region and a computer program for performing the method.

14 Claims, 5 Drawing Sheets

(51) Int. Cl.
*H01J 49/06* (2006.01)
*H01J 49/10* (2006.01)

(56) References Cited

U.S. PATENT DOCUMENTS

| | | | |
|---|---|---|---|
| 2008/0179515 A1* | 7/2008 | Sperline | G01N 27/622 250/290 |
| 2008/0179575 A1* | 7/2008 | Craig | E21D 21/008 254/251 |
| 2010/0044559 A1* | 2/2010 | Senko | H01J 49/061 250/282 |
| 2016/0203967 A1* | 7/2016 | Atkinson | H01J 49/061 250/282 |

* cited by examiner

METHOD FOR OPERATING AN ION GATE, DEVICE HAVING AN ION TRANSPORT REGION, AND COMPUTER PROGRAM

The invention relates to a method for operating an ion gate having at least a first electrode, a second electrode and a third electrode which are arranged in succession in a provided drift direction of ions to be influenced by the ion gate in such a way that, in the drift direction, the second electrode is arranged behind the first electrode and the third electrode is arranged behind the second electrode, wherein, by applying time varying potentials to one or more of the aforementioned electrodes, the ion gate is switched between a closed state, in which ions cannot drift through the ion gate in the provided drift direction, and an open state, in which ions can drift through the ion gate in the provided drift direction. Further, the invention relates to a device having an ion transport region and at least one field generating device having an ion transport region and at least one field generating device for moving the ions in a provided drift direction in the ion transport region by means of an electric field, wherein the ion transport region has an ion gate having at least a first electrode, a second electrode and a third electrode, which are arranged in succession in the provided drift direction of the ions in such a way that, in the drift direction, the second electrode is arranged behind the first electrode and the third electrode is arranged behind the second electrode, wherein the device further has a control device for controlling the ion gate, said control device being configured to carry out a method as claimed in any one of the preceding claims. The invention moreover relates to a computer program for carrying out the method.

In general, the invention relates to controlling an ion flow which should be controlled in a clocked manner, for example in an analysis appliance such as an ion-mobility spectrometer. A so-called ion gate can be used to influence the ion flow. In this context, the invention relates, in general, to the field of ion-mobility spectrometry and the associated appliances, i.e. of ion-mobility spectrometers and gas analysis devices formed therewith.

Such a gas analysis device with an ion-mobility spectrometer is described in WO 2015/091146 A1.

Ion-mobility spectrometers are appliances for the fast and highly sensitive analysis of trace gases, said ion-mobility spectrometers separating and identifying substances on the basis of the movement of their ions through a neutral gas under the influence of an electric field. Here, the so-called time-of-flight ion-mobility spectrometer represents a conventional embodiment; it measures the time that ions need to pass over a defined path. It consists of four main components—an ion source, which produces ions, an ion gate, which allows an ion packet to pass at periodic intervals, a drift path, along which the time-of-flight is measured, and a detector which records the incident ion flow. Since instances of ion packet broadening at the start time are directly reflected in scattering of the observed time-of-flight or in instances of ion packet broadening at the detector, and thus reduce the analytic capability, a fast ion gate represents an important component of every time-of-flight ion-mobility spectrometer. Consequently, an optimized ion gate would be of great interest to each of these devices. Inter alia, the ion gate is also referred to as gate or shutter; the transfer of ions from the ion source into the drift path is also referred to as injection.

The ion gate described in WO 2015/091146 A1, having the arrangement made of three successive electrodes, already has many advantages; in particular, the three-electrode structure allows a distortion of the field, produced by the field generating device, for transporting the ions to be minimized. However, the procedure described therein for operating the ion gate leads to discrimination against slower ion species; i.e., such slow ions are excluded from the analysis since they are often unable to pass the ion gate within the required time.

The invention is based on the object of specifying a method for operating an ion gate of the type described above, in which a discrimination against slower ions is minimized. Further, a corresponding device and a computer program to this end are intended to be specified.

This object is achieved by a method for operating an ion gate having at least a first electrode, a second electrode and a third electrode which are arranged in succession in a provided drift direction of ions to be influenced by the ion gate in such a way that, in the drift direction, the second electrode is arranged behind the first electrode and the third electrode is arranged behind the second electrode, wherein, by applying time varying potentials to one or more of the aforementioned electrodes, the ion gate is switched between a closed state, in which ions cannot drift through the ion gate in the provided drift direction, and an open state, in which ions can drift through the ion gate in the provided drift direction, wherein, in a switching cycle of the ion gate which comprises the open state and the closed state of the ion gate, two different closed states of the ion gate are produced by virtue of the ion gate being closed in a first closed state by applying a first potential difference between the second electrode and the third electrode and the ion gate being closed in a second closed state by applying a second potential difference between the first electrode and the second electrode.

Here, the invention unifies the following advantages:

There is no longer any discrimination, or at least no discrimination that is relevant in practice, against specific ion species. Slow ions are also able to pass the ion gate within the desired switching cycles of the ion gate and consequently can be used for the analysis.

The desired field profile within the ion transport region, i.e. the region which the ions are intended to pass through as a result of drift, is not distorted by the ion gate.

The ion gate has a mechanically simple construction and it can accordingly be manufactured in a simple and cost-effective manner. The ion gate can be operated with comparatively small electrical voltages, without this being accompanied by a restriction in the selection of usable ionization sources.

This is realized by the introduction of an additional switching state of the ion gate, namely the two different closed states. By applying the first potential difference between the second electrode and the third electrode, the ion gate is closed only on one side, namely in respect of a rear chamber formed between the second electrode and the third electrode. In this state, the ions are still able to pass a front chamber formed in front of the rear chamber between the first electrode and the second electrode. Accordingly, the ions are directly available at the central second electrode. If there is now a switch into the open state, the start of the injection of the ions into the further ion transport region occurs without retardation or discrimination. By subsequent switching into the second closed state, the ion gate can be closed in respect of the front chamber, i.e. between the first electrode and the second electrode. However, the ions, and also the slower ions, have already passed the second electrode at this point and are situated in a region in which they are no longer influenced by the closed state of the ion gate.

The continuous drift movement of the ions through the ion gate and the adjoining regions of the ion transport region of a corresponding device is also referred to as an ion flow. Closing the ion gate, i.e. setting the first closed state or the second closed state, is realized by producing a potential difference that blocks the ion flow at the respectively involved electrodes, i.e., firstly, the second electrode and the third electrode and, secondly, the first electrode and the second electrode. In the case of positive ions, a lower potential is produced at the second electrode than at the third electrode in the first closed state and a higher potential is produced at the second electrode than at the first electrode in the second closed state. In the case of negative ions, the potential difference is correspondingly produced in a reversed manner.

The invention advantageously makes use of the fact that two interstices between the electrodes exist between three electrodes arranged in succession, in particular three parallel electrodes, both of said interstices being able to be used to close the ion gate and hence to shutter the ions. An electrical potential at the central (second) electrode, which prevents the passage of ions through the front chamber of the ion gate, is also referred to as a second closing potential below. For positive ions, this is a more positive potential than that of the first electrode and it is a more negative potential for negative ions. Conversely thereto, there also exists a first closing potential of the central electrode which prevents the passage of ions through the rear chamber. For positive ions, this is a more negative potential than that of the third electrode and it is a more positive potential for negative ions. Here, the electrodes are numbered in succession in the direction of flight of the ions. Furthermore, there exists a passage potential, which lies between the potentials of the outer electrodes. Usually, this lies in the middle of the two, although this is not necessary. By way of a skilled change between these three potentials, it is possible to inject ions without discrimination. In the initial state, the first closing potential is applied to the central electrode such that the front chamber of the ion gate is already filled with ions as said ions are able to pass said chamber. Now, the central grid is switched to the passage potential and ions are consequently injected. Since ions are available directly at the central grid, the start of the injection is effectuated without retardation or discrimination. In order to complete the injection, the central grid is switched to the second closing potential. All ions in the front chamber are discharged and no further ions are able to pass the ion gate. However, the rear chamber remains passable, and so all ions which have already passed the central grid at this time are injected instead of being discharged again upon closure of the ion gate, as is the case in other ion gate principles. After all ions have left the rear chamber, the central grid is switched back to the first closing potential again and the ion gate is back in its initial state. No ions are able to pass the ion gate during this change since the front chamber no longer contains ions on account of the previously applied second closing potential.

Thus, although the ion gate physically has two large elimination regions, there is no longer any discrimination against slower ion species. This is achieved by virtue of the respectively effective elimination region being moved around the injected ion packet by appropriate wiring.

According to an advantageous development of the invention, provision is made, during a switching cycle of the ion gate, for the first closed state to be assumed first, followed by the open state and then the second closed state. This is advantageous in that the discrimination against slower ions is minimized.

According to an advantageous development of the invention, provision is made for the first closed state to be assumed again after the second closed state. As a result of this, a new switching cycle is started. Consequently, a switching cycle starts with the first closed state.

According to an advantageous development of the invention, provision is made for only the potential at the second electrode to be varied during a switching cycle of the ion gate. This is advantageous in that the method according to the invention can be easily realized from a circuitry point of view as only the potential at one electrode has to be varied. The other electrodes may be connected to fixed potentials, which may advantageously be selected in such a way that the same field strength is produced between the first electrode and the third electrode as in the regions, adjoining the ion gate in front and behind thereof, of a device, in which the ion gate is provided.

According to an advantageous development of the invention, provision is made for the changeable potential at one electrode of the ion gate or the changeable potentials at a plurality of electrodes of the ion gate to be at least intermittently constant in one, more or all switching states of the ion gate. This is advantageous in that the individual switching cycles can be clearly separated from one another and, accordingly, a distinction between the switching cycles is possible in a simple manner within the scope of the analysis of the ions forwarded through the ion gate in a clocked manner.

According to an advantageous development of the invention, provision is made for the changeable potential at one electrode of the ion gate or the changeable potentials at a plurality of electrodes of the ion gate to be constantly changed in the open state of the ion gate. Consequently, the changeable potential or changeable potentials need not only be switched in a virtually rectangular manner (steep slopes) and be kept constant therebetween. Instead, transition regions are also admissible, for example linear or nonlinear transitions between potential levels that are kept constant. This is advantageous in that the requirements on the needed circuit components need not be particularly high and consequently it is possible to use commercially available, cost-effective circuit elements such as transistors. The transients occurring during a switching process may, as a result of this, even be used in an advantageous manner for realizing the method according to the invention, as will still be explained in more detail below on the basis of exemplary embodiments.

The object set forth at the outset is further achieved by a device having an ion transport region and at least one field generating device for moving the ions in a provided drift direction in the ion transport region by means of an electric field, wherein the ion transport region has an ion gate having at least a first electrode, a second electrode and a third electrode, which are arranged in succession in the provided drift direction of the ions in such a way that, in the drift direction, the second electrode is arranged behind the first electrode and the third electrode is arranged behind the second electrode, wherein the device further has a control device for controlling the ion gate, said control device being configured to carry out a method of the type described above. The aforementioned advantages may also be realized hereby. By way of example, the control device may be embodied as an electronic control device.

The first electrode, second electrode and/or third electrode may be embodied as, for example, a ring electrode.

According to an advantageous development of the invention, the first electrode, the second electrode and/or the third electrode of the ion gate is embodied as a grid electrode. This is advantageous in that the ion gate can be easily realized from a mechanical point of view, while at the same time having a high efficiency when influencing the ion flow.

In particular, the first electrode, second electrode and/or third electrode of the ion gate may be embodied not as a ring electrode. Accordingly, electrically conductive material of the respective electrode is also situated in the interior of the ion transport region.

If the first electrode, the second electrode and/or third electrode is embodied as a grid electrode, such an electrode has a grid-like conductive structure, wherein the term grid or grid-like should be understood in the broadest sense in this case and said term comprises all embodiments in which the grid-like structure extends through the ion transport region, i.e. through the volume of the ion transport region, in contrast to, for example, a ring electrode which may be arranged on the outer circumference only. In particular, the grid-like conductive structure may be embodied as a planar structure, i.e. with a plane, conductive grid-like structure.

The method according to the invention and the device according to the invention may further be developed by virtue of the electric field produced by the electrodes of the ion gate having a substantially homogeneous embodiment between adjacent electrodes of the ion gate across a cross-sectional area of the ion transport region conceived to be perpendicular to the provided drift direction of the ions, i.e. by virtue of the electric field strength and/or the direction of the field lines being substantially unchanging over the cross-sectional area. As a result of this, unwanted field distortions are avoided and reliable opening and closing of the ion gate over the entire cross-sectional area is ensured. Adjacent electrodes of the ion gate are, firstly, the first electrode and the second electrode and/or, secondly, the second electrode and the third electrode.

According to an advantageous development of the invention, the device is embodied as an ion-mobility spectrometer. In this way, it is possible to carry out a gas analysis by means of the ion-mobility spectrometer, with precise analyses of substances, in which slow ions are involved, also being carried out.

The invention can be used both in the case of negative pressure and in the case of atmospheric or positive pressure. Accordingly, the invention is suitable for all types of ion-mobility spectrometers, regardless of whether they are operated at negative pressure, atmospheric pressure or positive pressure.

The object set forth at the outset is further achieved by a computer program having program code means, configured to carry out a method of the type described above when the method is executed on a computer. By way of example, the method can be executed on a computer of the control device for controlling the ion gate.

Figure 3:
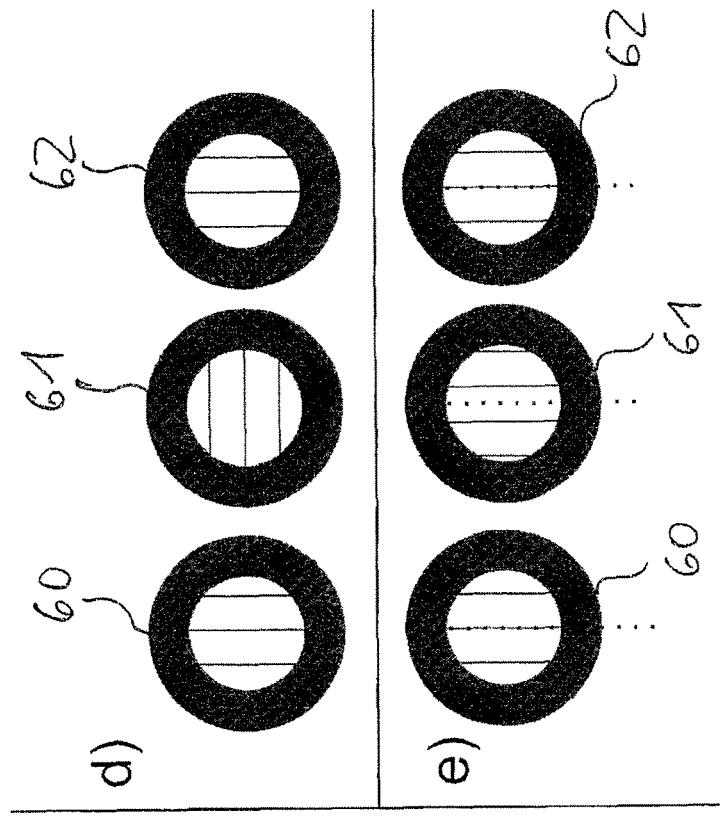
Figure 3:
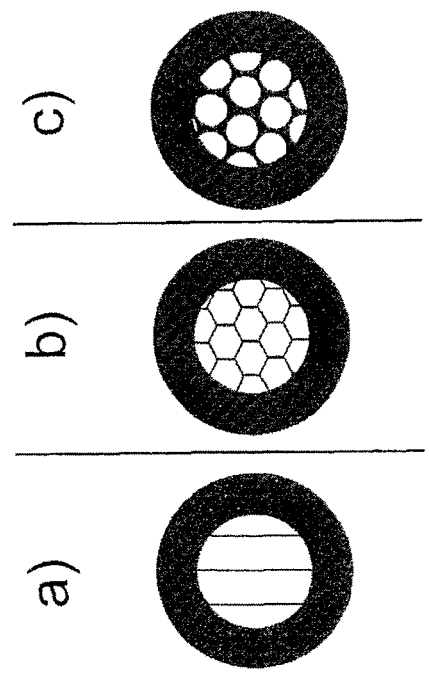
Figure 4:
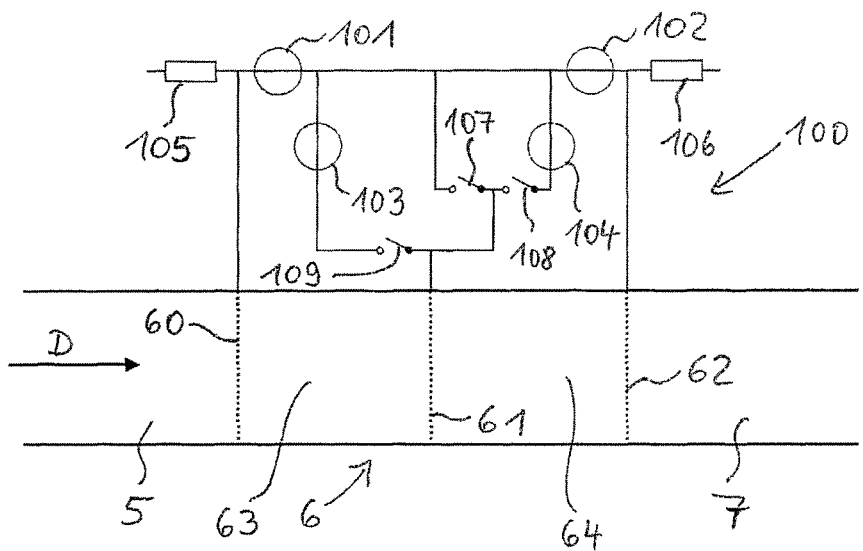
Figure 5:
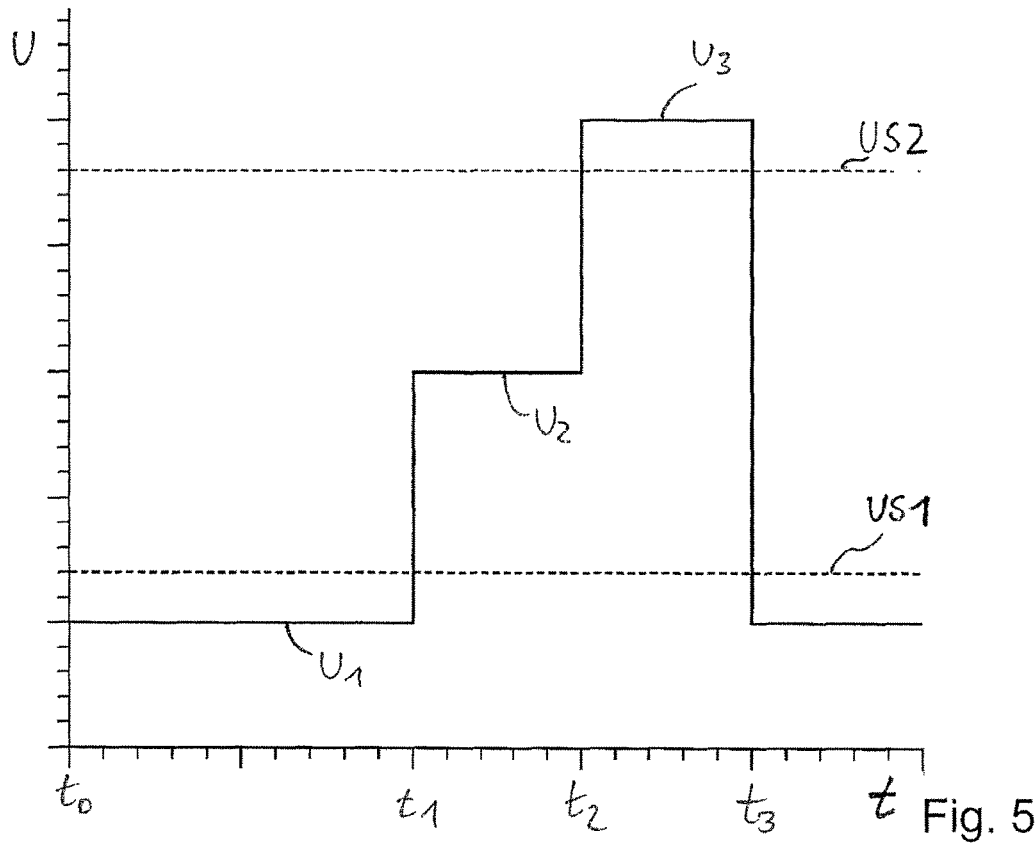
Figure 6:
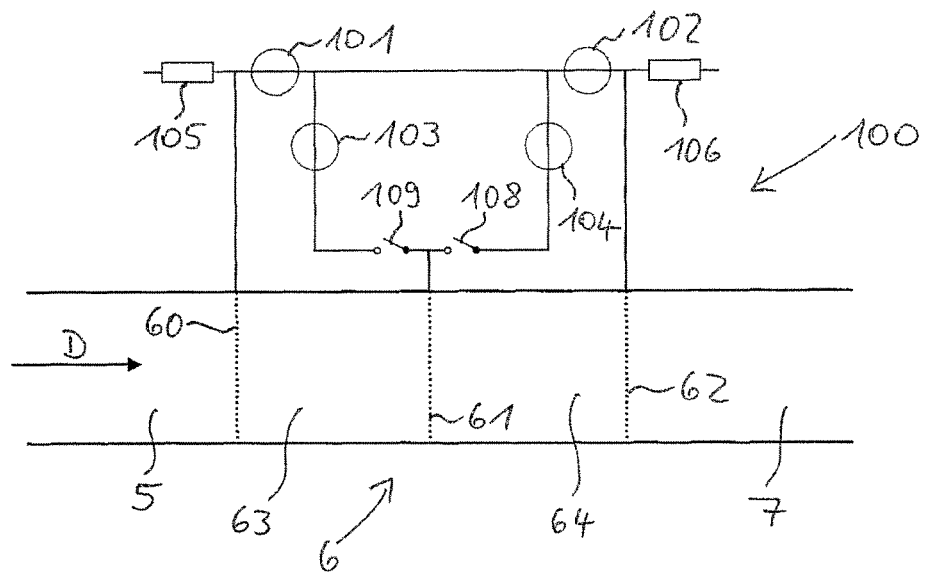
Figure 7:
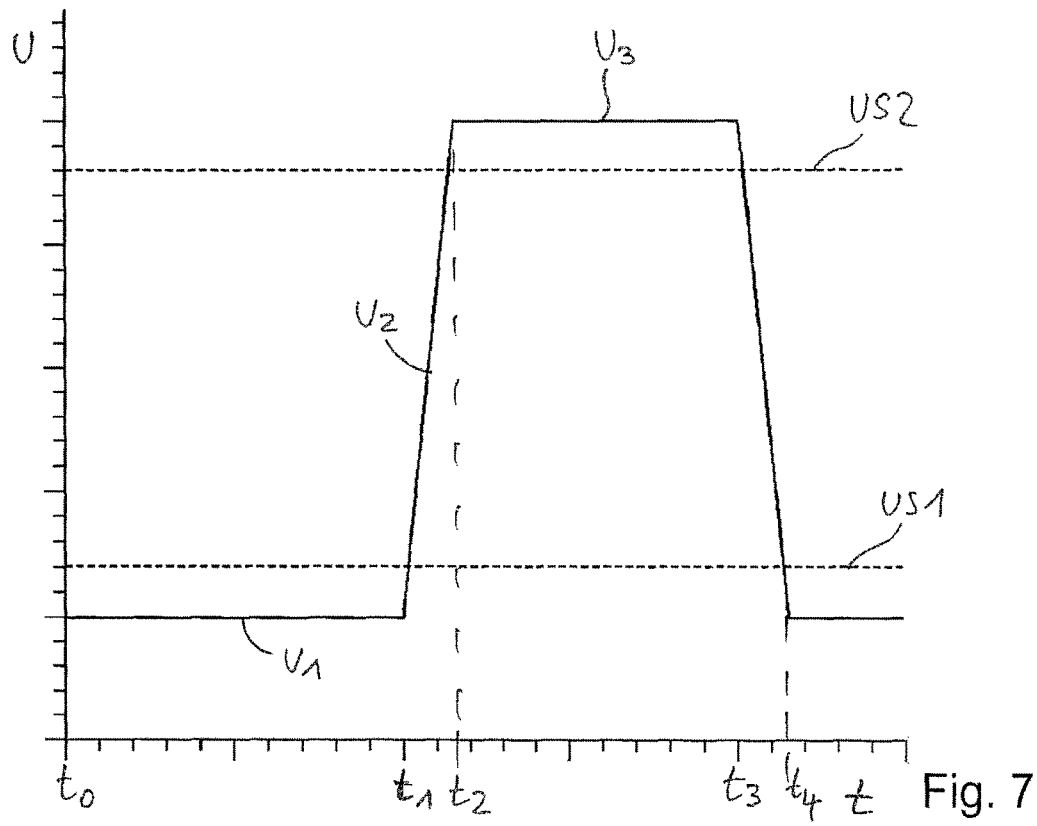

Using drawings, the invention will be explained in more detail below on the basis of exemplary embodiments. In the figures FIG. 1 shows, in a schematic illustration, the basic construction of a gas analysis device having an ion-mobility spectrometer and FIG. 2 shows the gas analysis device according to FIG. 1 with further components and FIG. 3 shows various embodiments of electrodes of the ion gate and FIG. 4 shows a first circuit arrangement for operating an ion gate and FIG. 5 shows a time chart for the operation of the ion gate according to FIG. 4 and FIG. 6 shows a second circuit arrangement for operating an ion gate and FIG. 7 shows a time chart for the operation according to FIG. 6.

In the figures, the same reference signs are used for elements that correspond to one another.

Figure 2:
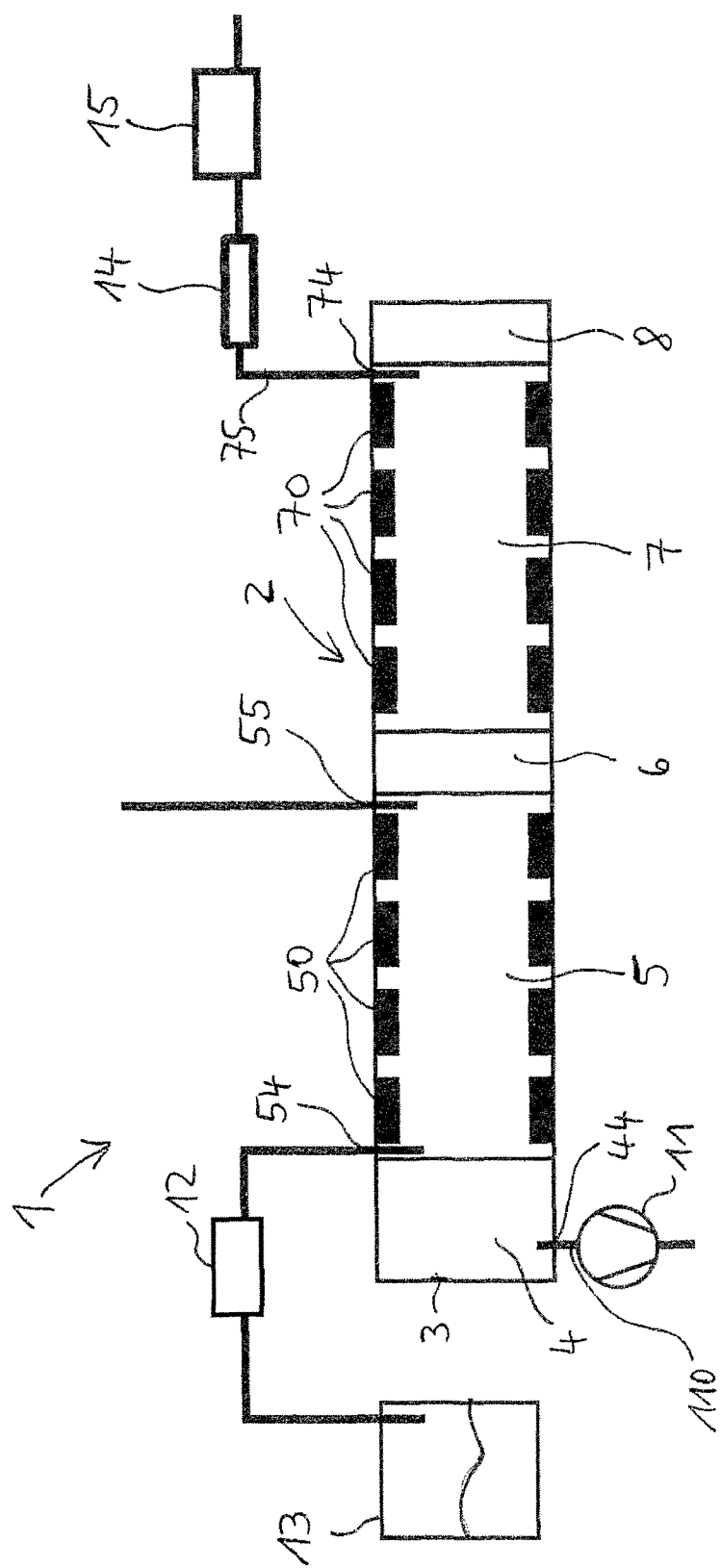

First of all, reference is made, in general terms, to the fact that FIG. 1 shows the gas analysis device or the ion-mobility spectrometer thereof in respect of the construction and the electrical wiring while FIG. 2 shows the same object in respect of the connections of the pressure lines and the supply of the gases as well as other substances. The described gas analysis device may advantageously have a combination of electrical wiring and the connections illustrated in FIG. 2; however, this is not reproduced in combination for the purposes of a better overview.

The gas analysis device 1 illustrated in FIG. 1 has an ion-mobility spectrometer 2 with an e.g. pipe-like or tubular housing body 3. The housing body 3 is subdivided into an ionization source region 4, a reaction chamber 5, an ion gate 6, a drift chamber 7 and an ion detector 8 which, as illustrated in FIG. 1, are arranged in succession in the aforementioned sequence. The ion detector 8, which may be embodied as e.g. a Faraday detector, for example in the form of a cup or in the form of a metal plate, is connected to an amplifier 9 that is connected to an electrical connector 80 of the ion-mobility spectrometer 2. The amplifier 9 amplifies the electric current that is supplied by way of the connector 80 and produced by the charges of the ions, such that a spectrogram 10 arises at the output of the amplifier 9. FIG. 1 further shows that electrodes 50, 70 of a first field generating device and a second field generating device are arranged, respectively, in the reaction chamber 5 and in the drift chamber 7. In the illustrated exemplary embodiment, the electrodes 50, 70 are embodied as ring electrodes which form a ring in the interior of the reaction chamber 5 and the drift chamber 7, respectively.

By way of example, the following embodiments of the ionization source region 4 of the gas analysis device 1 are advantageous:

a) An ionization with the aid of a corona discharge in a point-to-plane geometry. Here, a corona needle, which is introduced into the ionization source region 4 at the left-hand end side of the housing body 3, is connected to a voltage source via an electrical line, said voltage source providing a corona voltage. With its other connector, the voltage source is electrically connected to a grid electrode which is arranged in the ionization source region 4 in the interior of the housing body 3. A corona discharge is produced between the corona needle and the grid electrode, said corona discharge leading to an ionization of the gas molecules present there.

b) No grid electrode is provided in another embodiment of the ionization source region 4. Instead, the voltage source is connected to the ring electrode 50 of the reaction chamber 5 that is closest to the ionization source region 4, and to the corona needle. In this way, it is possible to achieve an ionization with the aid of a corona discharge in a point-to-ring geometry.

c) An electron emitter is arranged in the ionization source region 4 in another embodiment of the ionization source region 4, it likewise being possible to carry out an ionization of the gas using said electron emitter.

The ionization source of the gas analysis device 1 may be operated in a continuous or pulsed manner.

FIG. 2 shows various further components of the gas analysis device 1 that are connected to the housing body 3 of the ion-mobility spectrometer 2 via hollow lines. A suction connector 44, which is arranged at the housing body 3 in the ionization source region 4, but which may also, for example, be arranged in the region of the reaction chamber 5, is connected to a suction connector 110 of a negative pressure generating device 11, e.g. a pump. However, the invention may be used both in the case of negative pressure and in the case of atmospheric or positive pressure.

The water molecules required for the ionization in the ionization source region 4 may originate, for example, from the humidity of ambient air introduced into the gas analysis device. In particular in the case of relatively dry air, additional water may be guided into the housing body 3, for example directly into the reaction chamber 5, from a water tank 13 via a water supply connector 54. The supply of water, e.g. in the form of water vapor, may be effectuated directly from the water tank 13 via a hollow line connected to the water supply connector 54 or, as illustrated in FIG. 5, via a mass flow regulator 12 connected therebetween. By way of the mass flow regulator 12, it is possible to set the water supply in a defined manner and keep it constant.

The housing body 3 further has an analyte inlet connector 55 for supplying the analyte, i.e. the sample gas to be analyzed, from the surroundings. The analyte inlet connector 55 may open into, for example, the reaction chamber 5, in particular at the end of the reaction chamber 5 facing the ion gate 6.

The housing body 3 further has a drift gas supply connector 74 which is connected to a drift gas supply via a hollow line. In principle, various gases that behave in a chemically/physically neutral fashion with respect to the analyte ions, such as e.g. nitrogen or a noble gas, may be used as the drift gas. As a consequence of the relatively high nitrogen content of the ambient air, the latter may also be used directly as drift gas, and so FIG. 5 only illustrates a connection to the ambient air. A mass flow regulator 15 may be disposed upstream of the drift gas supply connector 74, as a result of which it is possible to regulate the supply of the drift gas and keep it constant. Further, a filter 14 may be disposed upstream of the drift gas supply connector 74 in order to clean the drift gas, which is advantageous particularly if use is made of ambient air as a drift gas.

The ionization source region 4, the reaction chamber 5, the region of the ion gate 6 and the drift chamber 7 may be pressure-connected among themselves, i.e. there is pressure equalization between these portions of the housing body 3. Thus, the desired negative pressure can be produced by the negative pressure generating device 11 and, at the same time, sample gas may be suctioned-in through the analyte inlet connector 55 and drift gas may be suctioned-in through the drift gas supply connector 74. Then, all suctioned-in gases are suctioned away by the negative pressure generating device 11 and discharged again.

In views a), b) and c), FIG. 3 shows different electrode forms of grid electrodes, as may be used as electrodes 60, 61, 62 of the ion gate 6 illustrated in FIGS. 4 and 6. In accordance with embodiment a), the electrode has stripe-shaped conductors which may extend vertically, horizontally or diagonally. According to embodiment b), the electrode has a hexagonal structure of the conductors. According to embodiment c), the electrode has a conductor arrangement with circular cutouts. Rectangular openings are also an advantageous embodiment.

View d) shows the three already mentioned electrodes 60, 61, 62 next to one another. It is possible to identify that the electrodes may be arranged in succession with different orientations of the stripe-shaped conductors in order to increase the effectiveness of the ion gate.

View e) shows the three already mentioned electrodes 60, 61, 62 next to one another. It is possible to identify that the electrodes 60, 61, 62 may also have stripe-shaped conductors that are arranged mutually offset from one another, as clarified by the axis of symmetry represented by the dotted line. In an advantageous embodiment, the holes of the hexagonal or circular arrangements may be offset from one another in order to increase the effectiveness.

The views reproduced in FIG. 3 show the electrodes in a viewing direction which corresponds to the drift direction of the ions illustrated in FIGS. 4 and 6.

FIGS. 4 and 6 in each case provide a magnified illustration of that part of the ion-mobility spectrometer in which the ion gate 6 is arranged. In part, it is possible to further identify the reaction chamber 5 and the drift chamber 7. The arrangement of the reaction chamber 5, the portion provided with the ion gate 6 and the subsequent portion having the drift chamber 7 is also referred to as ion transport region of the device. The ions move with a provided drift direction D through the ion transport region, or they are prevented from doing so intermittently by the ion gate 6.

The ion gate 6 has three electrodes arranged in succession in the drift direction D, namely, as seen in the drift direction, a first electrode 60 first, a second electrode 61 therebehind and a third electrode 62 therebehind. The electrodes 60, 61, 62 are electrically connected to an electronic control device 100. The electric control of the electrodes of the ion gate within the meaning of the method according to the invention is effectuated by way of the control device 100. To this end, the control device 100 has a computer, for example in the form of a microprocessor or microcontroller.

Two chambers 63, 64 of the ion gate 6 are formed by the three electrodes 60, 61, 62. On account of the selected illustration and the drift direction D provided here in an exemplary manner, the chamber 63 is also referred to as front chamber and the chamber 64 is also referred to as rear chamber. By way of an appropriate actuation of the electrodes 60, 61, 62 with different potentials, it is possible to operate the ion gate 6 in two different closed states, namely in a first closed state, in which the rear chamber 64 is blocked, and in a second closed state, in which the front chamber 63 is blocked. In this context, "blocked" means that the ion flow cannot pass the ion gate 6 or the blocked chamber in the drift direction D. Rather, the ions are absorbed in the respective chamber.

The circuit arrangement of the control device 100 for the electrical supply of the electrodes 60, 61, 62 may be formed, as illustrated, by a series connection of two voltage sources 101, 102 and resistors 105, 106. Here, the first electrode 60 is connected to a connection point between the resistor 105 and the voltage source 101. The third electrode 62 is connected to a connection point of the voltage source 102 and the resistor 106. Accordingly, the first electrode 60 and the third electrode 62 are connected to a constant electrical potential. Only the central, second electrode 61 may be switched in respect of its potential. To this end, provision is made of the illustrated arrangement made up of two voltage sources 103, 104 and switches 107, 108, 109. By way of the switch 107, the second electrode 61 may be connected to an intermediate potential which is defined by the connection point between the voltage sources 101, 102. By closing the switch 108, the second electrode 61 may be placed at a first higher potential, said first higher potential being defined by the voltage source 104. Depending on the ion polarity, it may also be lower, for example $U_1$ in FIG. 5. By closing the switch 109, the second electrode may be placed at a third, even higher potential (or even lower potential in the case of the other ion polarity) which is defined by the voltage source 103. Accordingly, only one of the switches 107, 108, 109 is closed at any one time. The switchover between opening and closing the switches is effectuated in such a synchronized manner that the second electrode 61 is connected to one of the three mentioned potentials practically without interruption.

FIG. 5 shows, in an exemplary manner, a switching cycle of the ion gate with the three aforementioned states, namely the open state and two different closed states. Here, the potential U applied to the second electrode 61 is plotted over time. The switching cycle begins at a time $t_0$. A potential $U_1$, which, as may be identified, is relatively low and, in particular, lies below a lower threshold US1, is applied from this time until a time $t_1$. In combination with the potentials applied to the first electrode 60 and the third electrode 62, a potential difference between the second electrode and the third electrode arises, said potential difference blocking the ion gate in the rear chamber 64; i.e., the ion flow can still traverse the front chamber 63 but can no longer traverse the rear chamber 64. No such blocking effect arises in this state in respect of the potential difference between the first electrode 60 and the second electrode 61.

The ion gate 6 is switched into the open state at the time $t_1$ by virtue of the potential at the second electrode 61 being raised to a value above the lower threshold US1, namely to the potential $U_2$ illustrated there. Here, the potential $U_2$ may be placed in the middle between the lower threshold value US1 and an upper threshold value US2, but this is not mandatory. What is decisive is that such a potential is set that the ion gate transitions into an open state in respect of all electrodes and the ions are able to pass the ion gate.

At the time $t_2$, the ion gate is transferred into the second closed state by virtue of the potential at the second electrode 61 being raised to a value above an upper threshold value US2, illustrated here in an exemplary manner by a potential $U_3$. Now, the front chamber 63 is blocked; the rear chamber 64 is open. As a result, the ion gate is in the second closed state.

At a time $t_3$, the potential at the second electrode 61 is lowered again to a value below the lower threshold value US1, as a result of which the ion gate is switched from the second closed state into the first closed state; i.e., the front chamber 63 does not produce a blocking effect for the ions, but the rear chamber 64 does. Now, a new switching cycle of the ion gate starts, said switching cycle being able to proceed in the above-described manner.

The voltage sources and/or switches reproduced in an exemplary manner in FIGS. 4 and 6 may also be realized by other components, such as e.g. controlled transformers, to which, for example a continuously increasing current may be applied in order, at the output side, to produce certain at least approximately constant potentials. The illustrated switches 107, 108, 109 may be embodied as mechanical switches, e.g. relays or contactors, or, advantageously, as semiconductor switches, e.g. in the form of transistors such as, for example, IGBTs or other field-effect transistors.

FIG. 6 shows a circuit arrangement which is comparable to that in FIG. 4 apart from the differences explained below.

In contrast to FIG. 4, the line branch having the switch 107, by means of which the second electrode 61 is directly connectable to the potential between the voltage sources 101, 102, is missing. Consequently, only the switches 108, 109 remain. In order nevertheless to be able to produce an intermediate potential between the threshold values US1, US2 at the second electrode 61, a transient profile between the lower potential $U_1$ and the upper potential $U_3$ is used in a targeted manner, said profile being connected to a certain rise time. By way of example, if use is made of commercially available semiconductor switches for the switches 108, 109, use can be made of the rise time or fall time between the potentials $U_1$ and $U_3$, which occurs in any case in such a circuit arrangement. This emerges from the restricted conductivity of the semiconductor switches in combination with capacitances in the circuit arrangement that are present in any case, such as e.g. parasitic capacitances of the feed cables. Optionally, this effect can still be adapted to a desired value of the rise time or the fall time by adding in one or more resistors and/or capacitors.

As illustrated in the time chart in FIG. 7, which belongs to the circuit arrangement according to FIG. 6, an e.g. ramp-shaped profile of the potential U emerges between the times $t_1$ and $t_2$, and also between the times $t_3$ and $t_4$, when switching between the switches 108, 109. By way of example, the switch 108 is closed and the switch 109 is simultaneously opened at the time $t_1$. There is a rise in the potential until the time $t_2$. At the time $t_3$, the switch 109 is closed and the switch 108 is opened. There is a fall in the potential at the second electrode 61 until the time $t_4$.

As can be identified, in this switching cycle too, the states of first closed state, open state and second closed state are run through in the specified sequence. The ion gate is open for as long as the potential at the second electrode 61 lies in the range between the lower threshold US1 and the upper threshold US2.

As can be identified, the circuit arrangement according to FIG. 6 may also be realized using a single switch by virtue of using a changeover switch. In the embodiment according to FIG. 4, it is possible to use e.g. a triple changeover switch instead of the three individual switches.

The invention claimed is:

1. A method for operating an ion gate having at least a first electrode, a second electrode and a third electrode which are arranged in succession in a provided drift direction of ions to be influenced by the ion gate, wherein in the provided drift direction the second electrode is arranged behind the first electrode and the third electrode is arranged behind the second electrode, in a way that a first chamber is formed between the first and second electrode and that a second chamber is formed between the second and third electrode, comprising:

applying time varying potentials to one or more of the first, second, and third electrodes to switch the ion gate between an open state, in which a first potential difference between the first and second electrode allows ions of one of a positive or negative polarity to move through the first chamber in the provided drift direction and a second potential difference between the second and third electrode allows ions of the one of a positive or negative polarity to move through the second chamber in the provided drift direction, a first closed state, in which a third potential difference between the first and second electrode allows ions of the one of a positive or negative polarity to move through the first chamber in the provided drift direction, but a fourth potential difference between the second electrode and the third electrode prevents ions of the one of a positive or negative polarity to move through the second chamber in the provided drift direction, and a second closed state, in which a fifth potential difference between the first electrode and the second electrode prevents ions of the one of a positive or negative polarity to move through the first chamber in the provided drift direction, but a sixth potential difference between the second and third electrode allows ions of the one of a positive or negative polarity to move through the second chamber in the provided drift direction.

2. The method as claimed in claim 1 wherein during a switching cycle of the ion gate, the first closed state is assumed first, followed by the open state and then the second closed state.

3. The method as claimed in claim 2 wherein the first closed state is assumed again after the second closed state.

4. The method as claimed in claim 1 wherein only a potential of the time varying potentials at the second electrode is varied during a switching cycle of the ion gate.

5. The method as claimed in claim 1 wherein one or more of the time varying potentials at one or more of the first, second and third electrodes of the ion gate are at least intermittently constant in one, more or all switching states of the ion gate.

6. The method as claimed in claim 1 wherein one or more of the time varying potentials at one or more of the first, second and third electrodes of the ion gate are constantly changed in the open state of the ion gate.

7. A device, comprising:
an ion transport region;
at least one field generating device for moving the ions in a provided drift direction in the ion transport region by means of an electric field, wherein the ion transport region has an ion gate having at least
a first electrode,
a second electrode, and
a third electrode,
wherein the first, second and third electrodes are arranged in succession in a provided drift direction of ions, wherein in the provided drift direction, the second electrode is arranged behind the first electrode and the third electrode is arranged behind the second electrode; and a control device for controlling the ion gate, said control device being configured to carry out a method as claimed in claim 1.

8. The device as claimed in claim 7 wherein one or more of the first electrode, the second electrode, and the third electrode of the ion gate is embodied as a grid electrode.

9. The device as claimed in claim 7 wherein the device is embodied as an ion-mobility spectrometer.

10. A non-transitory storage medium encoded with a computer program executable on a computer and configured to carry out a method as claimed in claim 1.

11. The method of claim 1, wherein the first, second and third electrodes are not ring electrodes.

12. The method of claim 1, wherein the first, second and third electrodes are grid electrodes.

13. The device of claim 7, wherein the first, second and third electrodes are not ring electrodes.

14. The device of claim 8, wherein the first, second and third electrodes are grid electrodes.

* * * * *